(12) United States Patent
Chou

(10) Patent No.: US 8,945,916 B2
(45) Date of Patent: Feb. 3, 2015

(54) DEVICE AND METHOD FOR PHOTOSYNTHETIC CULTURE

(76) Inventor: David Shih-Wei Chou, Grand Forks, ND (US)

(*) Notice: Subject to any disclaimer, the term of this patent is extended or adjusted under 35 U.S.C. 154(b) by 336 days.

(21) Appl. No.: 13/161,462

(22) Filed: Jun. 15, 2011

(65) Prior Publication Data

US 2011/0306121 A1 Dec. 15, 2011

Related U.S. Application Data

(60) Provisional application No. 61/422,184, filed on Dec. 12, 2010, provisional application No. 61/355,121, filed on Jun. 15, 2010.

(51) Int. Cl.
| | |
|---|---|
| *C12M 1/00* | (2006.01) |
| *C12R 1/89* | (2006.01) |
| *C12N 1/12* | (2006.01) |
| *C12M 1/12* | (2006.01) |

(52) U.S. Cl.
CPC ............... *C12M 21/02* (2013.01); *C12R 1/89* (2013.01); *C12N 1/12* (2013.01); *C12M 23/04* (2013.01); *C12M 39/00* (2013.01); *C12M 41/08* (2013.01)
USPC ..................................................... 435/292.1

(58) Field of Classification Search
CPC .................................................... C12M 21/02
USPC ..................................................... 435/292.1
See application file for complete search history.

(56) References Cited

U.S. PATENT DOCUMENTS

| | | | |
|---|---|---|---|
| 3,959,923 | A | 6/1976 | Selke |
| 5,162,051 | A | 11/1992 | Hoeksema |
| 6,509,188 | B1 | 1/2003 | Trosch et al. |
| 7,220,018 | B2 | 5/2007 | Crabb |

(Continued)

FOREIGN PATENT DOCUMENTS

| | | | | |
|---|---|---|---|---|
| JP | 08-009809 | * | 1/1996 | ............. A01G 33/00 |
| JP | 08-009809 A | | 1/1996 | |
| WO | WO 2009/116852 A1 | | 9/2009 | |
| WO | WO 2009-116853 A1 | | 9/2009 | |

OTHER PUBLICATIONS

Postein, "Design principles of photo-bioreactors for cultivation of microalgae," Eng. Life Sci. 2009, 9. No. 3, 165-177.

(Continued)

*Primary Examiner* — Jonathan Hurst
(74) *Attorney, Agent, or Firm* — Knobbe Martens Olson & Bear LLP

(57) ABSTRACT

A device and system for growing of a photosynthetic culture is provided which employs one or a plurality of vertically disposed photopanels having interior cavities configured for holding liquid and the photosynthetic culture such as algae. Interior surfaces are enhanced in size by projections defined by deformation in sidewalls of the photopanels. The projections communicate between the sidewalls also providing structural integrity to the photopanel and allowing for thinner sidewalls and increased light transmission therethrough. The system may employ a support rack and pivotal mount to each such photopanel to allow positioning adjacent to each other in rows. Pivoting during different lighting conditions afforded the racked photopanels provides a manner to reduce light blockage to individual photo panels from adjacent photopanels.

20 Claims, 9 Drawing Sheets

(56) References Cited

U.S. PATENT DOCUMENTS

| | | |
|---|---|---|
| 7,374,928 B2 | 5/2008 | Trösch |
| 2008/0160591 A1 | 7/2008 | Willson |
| 2008/0286851 A1 | 11/2008 | Whitton |
| 2009/0011492 A1* | 1/2009 | Berzin ............... 435/257.1 |
| 2010/0028976 A1 | 2/2010 | Hu |
| 2011/0065157 A1 | 3/2011 | Gorny |
| 2011/0104790 A1 | 5/2011 | Kassebaum |
| 2011/0151507 A1* | 6/2011 | van Walsem et al. ........... 435/41 |

OTHER PUBLICATIONS

Chen et al., *"Review of the biological and engineering aspects of algae to fuels approach,"* Int. J. Agric. & Biol. Eng., vol. 2 No. 4, pp. 1-30, Dec. 2009.

International Search Report and the Written Opinion issued on Dec. 22, 2011 in the corresponding PCT Application No. PCT/US2011/040592.

Image capture of Subitec website (http://en.subitec.com/microalgae-technology/fpa-reactors.html), accessed Feb. 16, 2012.

\* cited by examiner

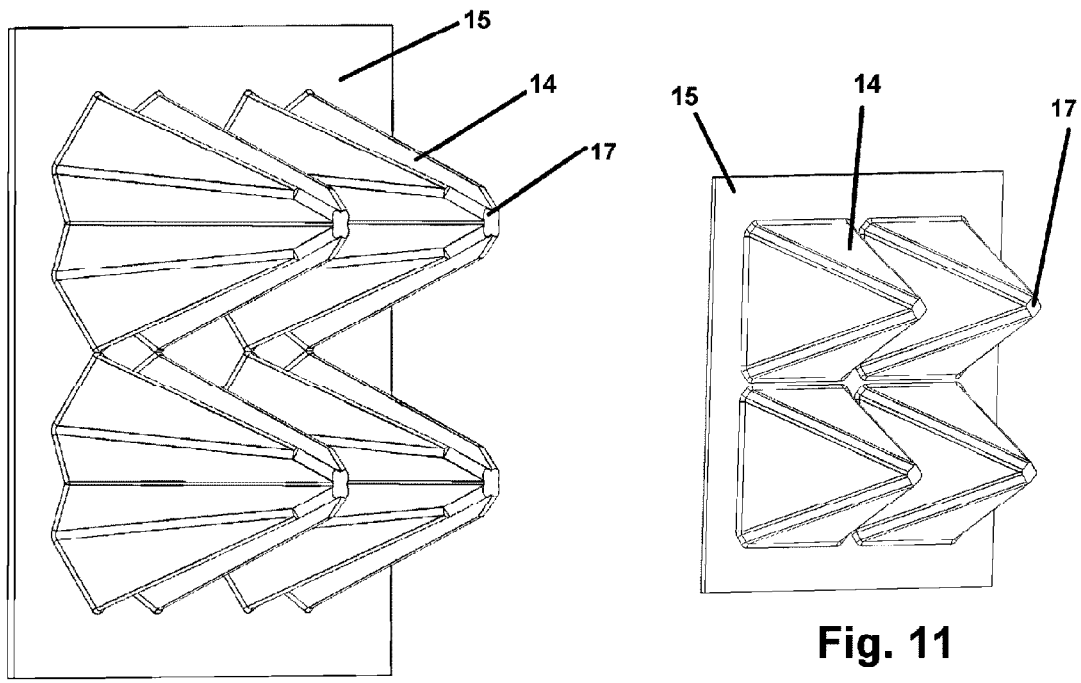
Fig. 10
Fig. 11
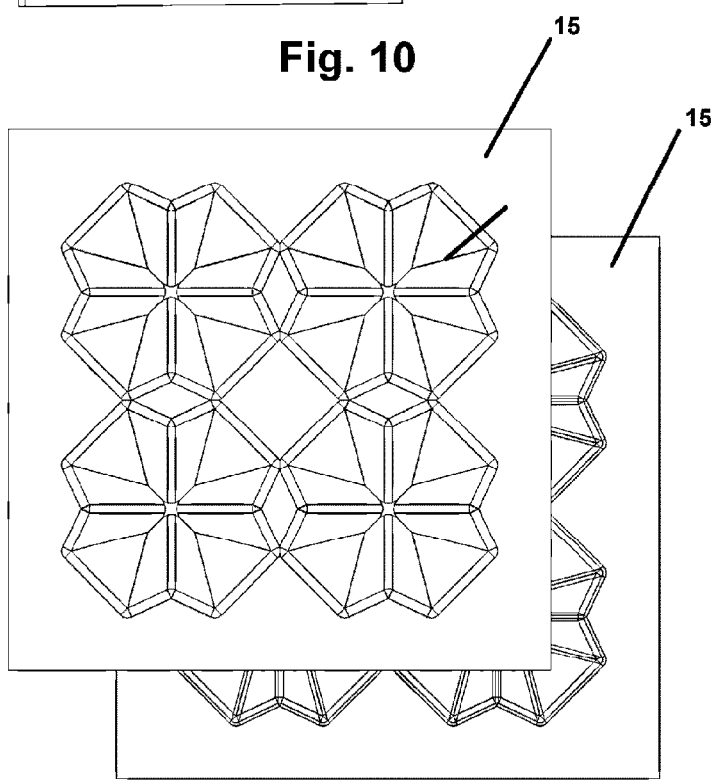
Fig. 12

DEVICE AND METHOD FOR PHOTOSYNTHETIC CULTURE

This application claims the benefit of U.S. Provisional Application Ser. No. 61/422,184 filed on Dec. 12, 2010 and U.S. Provisional Application Ser. No. 61/355,121 filed on Jun. 15, 2010, both applications respectively incorporated herein in their respective entirety, by reference thereto.

FIELD OF THE INVENTION

The disclosed device and method herein relates to photosynthetic cell cultures, as it is applied to production of biomass as well as CO2 recycling or sequestration and waste water mitigation. More specifically, the disclosed device and method relate to the commercialization of phycology for industrial scale application. The method and apparatus for the system herein, represents a new and improved system to scale up algae production into industrial quantities which employs novel vertically-oriented photosynthetic photobioreactors or photopanels and method of culture and deployment strategy.

The disclosed system optimizes the available solar energy for photosynthesis through the distribution of scattered solar irradiance over a dramatically expanded surface area whereby the solar light intensity is reduced toward or into optimal intensity range for algal photosynthesis. The disclosed photopanel device is highly adaptable to accommodate the diversity of algae strains, as well as geographic and seasonal variation utilizing common inexpensive and recyclable material. The disclosed photopanel design is especially adaptable for suspended as well as adherent algal cultures for the purpose of producing algal oil for use as biofuel. The new disclosed photopanel design addresses very specific nearly mutually exclusive culture needs for algal replication vs. algal fatty acid synthesis in the same continuous culture with ultra high cell concentrations.

BACKGROUND OF THE INVENTION

Current human dependence on fossil or petroleum fuel as a limited resource has prompted development of alternative renewable energy sources. $CO^2$ emitted from the burning of fossil fuel, as a green house gas and primary cause of global warming, adds further urgency. The United States, it is estimated, consumes more than 43 billion gallons per year of diesel fuel for transportation plus a multiple of this amount for gasoline and other oil-based fuels. In effort to provide fuel using sources other than so called fossil or petroleum derived fuels, biodiesel is derived from vegetable oil and animal fats. Corn based ethanol is now blended with gasoline at higher percentages. Current development of biofuels such as ethanol from corn requires extensive amounts of land and water. The use of food stuff in generation of transportation fuel has caused pricing pressure on agricultural commodities.

Photosynthesis converts the solar electromagnetic energy into stored chemical energy in long carbon chains by assembling carbon from $CO^2$. Photosynthesis is the primary process on earth that sequesters and recycles $CO^2$. Microalgae are the most photosynthetically efficient organisms. Algae, as a source of biofuel, have long been studied. The last energy crisis in the 1970's fueled research in alternative energy sources. A substantial amount of knowledge has been amassed by the U.S. Department of Energy's Aquatic Species Program. Algae may be grown in impaired water. Algae is highly efficient in photosynthesis with amazing rates of replication. Some algal strains can double every 4 to 6 hours. Algae when grown in certain conditions such as nitrogen-deficient culture can synthesize and accumulate fatty acids to levels greater than half of its dry weight. The algal fatty acids or oils are capable of being and currently is refined into jet fuel for the US Navy. However, cultivation systems allowing for scale up of algae culture from laboratory quantities to an industrial scale of production have heretofore been challenging. Conventionally, such algal cultivation systems can be separated into two categories: open vs. closed. Each conventional categories has pros and cons.

The open cultivation systems are "open" to the environment and the most common current form can be described as large raceway ponds. Such open ponds are the least expensive to build and operate. As such, open ponds was advocated by the ASP findings to compete with fossil fuel. However, raceway ponds require high water use due to constant evaporation. Open ponds offer sub-optimal light intensity control. Open ponds are prone to contamination from wild type strains overwhelming the desired cultured strains being propagated. Additionally, this type of open culture, being unprotected, is subject to predators which feed on algae. Large cultured ponds could be decimated in a few days by such predators. While large amount of resources are being funneled into designing or genetically modifying algae to improve yield and overcome the above-noted short comings of open ponds, it is unlikely that public opinion would allow the use of genetically altered mutant strains in open system with the accompanying risk of uncontrollable environmental contamination. Geographic limitations such as temperature and solar irradiance as well as land requirements are additional limitations.

Closed systems or photobioreactors are designed to address all of these limitations and concerns of the open pond systems to varying degrees. However, one of the major challenges is efficient utilization of solar irradiance. Solar irradiance as experienced at the earth's surface is highly variable, dependent of geophysical factors such as seasonal, daily and atmospheric variations. The phenomenon of "self shading or self shadowing" further complicates the utilization of solar irradiance. As light penetrates an algal culture, photons are absorbed by chlorophyll, decreasing the light intensity. This "self shading" is exaggerated in high cell concentration culture with high chlorophyll concentration. In fact, light does not penetrate very far at all in high cell concentration cultures, just a few millimeters. Optimal light intensity for algal photosynthesis has been demonstrated to be a small fraction of direct bright solar irradiance, in the range of 10%. An algal culture in an open pond commonly experiences a detrimental superficial culture layer in which the excessively high light intensity of direct solar beam causes photoinhibition, cell damage and possibly cell death. Through "self shading", the high toxic level of light intensity is attenuated by chlorophyll absorption in the initial superficial "toxic" layer whereby a middle layer of culture experience "optimized" light intensity for algal photosynthesis. Any deeper layer of culture, as light intensity further attenuates, fails to receive sufficient light to drive algal photosynthesis.

Current art or culture systems, open or closed, rely on the strategy of cell movement in and out of the various conceptual light zones: 1) superficial toxic, 2) middle optimal and 3) deep deficient zones. Algal cells may move into the potentially toxic superficial layer to absorb photons for only milliseconds to microseconds before leaving the zone so damaging radicals do not build up. Current art of open ponds utilize large paddles to create stirring and current flow and typical closed systems such as tubular systems utilize pumps. Much of the current flow are laminar flow, parallel to the conceptual light zones described above, instead of more efficient turbulent flow in moving cells perpendicular through the light zones. Furthermore, algal movement through the pumps may experience shear injury at higher velocities. Despite the efficiencies gained with current closed systems, in general, photobioreactors are not cost effective to compete with fossil fuels in normal market conditions. The least expensive of the current closed systems are simple plastic bags with little structure. As these batch type cultures grow and chlorophyll content increases, larger and larger proportions of the culture in the middle does not receive enough light for photosynthesis, limiting achievable cell concentrations.

One prior art example of a closed system is that of U.S. Pat. No. 6,509,188 (Trosch) which teaches a photobioreactor having a reactor chamber formed of transparent material and having recesses and projections adapted to increase the reactor surface area with tubular projections and extensions. However, the Trosch patent construction does little to increase the structural integrity of the formed reactor panels, and lacks a narrow cross sectional area for limiting diffusion of nutrients to different height levels for the establishment of a nutrient gradient within the reactor.

As such, there exists an unmet need for algae culture systems which has a reasonable capital and operational cost to compete with crude oil under normal market conditions. Such a system should be able to continuously achieve an ultra-high cell concentration algal culture. Such a system should provide a structure and deployment thereof which provides a more even means to communicate solar and artificial radiation evenly and controllably. Further, such a system should inherently include means to prevent or limit bio-fouling or deposition of bio-film and should employ components which serve to expand surface area of the photobioreactor inner enclosure and concurrently provide a means for enhanced structural integrity. Additionally, such a system should employ a reactor which is structurally enhanced and which provides a stability of the desired high surface area to volume ratio of the algal culture as well as the desired small cross sectional area available which provides a means for limiting diffusion of nutrient to different height levels for establishing a nutrient gradient.

SUMMARY OF THE INVENTION

The device and method herein disclosed provides a novel means for the cultivation of algae to optimize conversion of available solar electromagnetic energy to stored chemical energy through the biochemical process of photosynthesis. Possible application includes but not limited to the production of biomass for feed stocks, fertilizers, nutriceuticals, as well as water treatment and $CO^2$ sequestration. One of the primary objectives of the disclosed novel system is to optimize growth conditions in an economical process that makes algal biofuel a competitive, alternative renewable fuel.

The global strategy is to achieve ultra-high cell concentration algal culture. By achieving ultra-high cell concentration, the volume of cell culture medium and the material needed to enclose the medium are minimized. The higher the cell concentration, the higher solar intensity the algal culture could utilize with cell movement. Achieving ultra-high cell concentration will also lessen the cost of algal separation from the culture media at harvest. To facilitate ultra-high cell concentration culture, the algae culture will take on a high surface area to volume ratio by applying a new construct of "hollow trabeculae" in the photopanel design. All surface area of the algal culture will be exposed to light source. The high surface area to volume ratio of an algal culture will minimize the number of cells potentially experiencing the "deep light-deficient zone" for an extended period of time. As a culture increases in cell concentration, the "self shading" phenomenon causes less and less light penetration so more and more cells closer and closer to the light exposed culture surface area experience insufficient light. In essence, the third theoretic light-deficient zone increases as the first two layers decrease. The "self-shading" mechanism therefore limits overall culture growth as well as limiting the cell number concentration achieved in the algal culture. Supportive artificial light for baseline night time photosynthetic activity may be applied to support oxygen requirements for algal night time respiration (to be expanded later under methods herein). The material selected to enclose the medium, should be common, transparent, flexible, inexpensive, and preferably recyclable. The system should be highly adaptable to accommodate the diversity of photosynthetic organisms and organelles as well as geophysical conditions.

More specific objectives of the disclosed novel system and the strategies applied are as follows: Optimal photosynthetic utilization of available solar irradiance is sought by applying the dictum of the Hippocratic Oath, "First do no harm". The high light intensity of direct solar beam is toxic to algal cells causing photoinhibition, cell damage and possible death, all of which are energetically expensive, lowering the light use efficiency. In essence, the strategy seeks to limit the first theoretic superficial toxic zone. The novel system seeks to limit direct solar irradiance and more effective use of scattered light. Scattered or indirect natural light is much closer to optimal light intensity for algal photosynthesis. This is largely achieved by simply orienting vertically disposed photopanels substantially parallel to the solar beam all hours of the day, rotating them with the movement of the sun across the sky. This allows solar beams to evenly penetrate the algae farm to be scattered and reflected by surface treatment of the ground. The top portion of the vertically disposed algae panels would receive atmospherically scattered light and the bottom portion of the vertical algae panels would receive scattered and reflected light off the ground treatment. The atmospherically scattered light experienced by the upper portion of vertically oriented photopanels is surprisingly consistent within a smaller light intensity range, irregardless of sunny vs. overcast, cloudy days. The light intensity from direct spectral solar beam can be dialed up by angling the photopanels a few degrees off parallel with the solar beam, to match the photosynthetic capacity of the algae culture. This application or strategy may seem simple, but not obvious, as it may be counter intuitive that less light is more. Increased algal culture surface area, distribution and reduction of light intensity as well as the structure to maintain a high culture surface area to volume ratio are all achieved by the application of a novel construct, "hollow trabeculae," to be further described under Photobioreactor Structure below.

High light conditions in which the scattered and redistributed light is still above optimal algal photosynthetic light intensity, the strategy of cell movement through the various conceptual toxic, optimal and deficient light zones, as previously described are applicable. This mechanism is even optimized by high cell concentration culture because exaggerated "self-shading" causing less light penetration, effectively decreasing the thickness of the first two theoretical zones or layers of light conditions. Algal cells would therefore experience the different zones with little displacement. Algal cells could oscillate between light and dark conditions rapidly. The stirring of the cells is achieved by bubbling, instead of energy requiring large paddles as in open raceway ponds or fluid pumps in closed tubular systems. CO2-rich gases such as flue gas from combustion of natural gas or coal are administered through a sparger at the bottom of the photopanel as a primary nutrient. The gas bubbles serve an additional function of cell agitation as it rises. Since CO2 utilization for photosynthesis is proportional to available light, increased light source requires more CO2 delivery or higher bubbling rate, which translates to a higher rate of agitation. In another words, higher light conditions could be titrated with higher bubbling rates delivering the higher requirement for CO2. The predominant turbulent flow caused by bubbling is much more efficient in moving cells perpendicular to the light zones.

An even more specific objective towards development of algal biofuel is accommodating the mutually exclusive needs for algal cell replication vs. algal fatty acid synthesis and accumulation. In nitrogen-rich culture medium, algal protein synthesis readily occurs. Excess energy is stored in more immediately available energy storage forms such as carbohydrates to drive processes of cell growth and cell replication. In the absence of nitrogen, protein synthesis is limited and cell growth and replication is inhibited. Excess energy is instead driven towards long term storage in the form of fatty acids. In current production of algal biomass, the whole algae cell is harvested. Cell harvest necessitates cell replication to maintain a stable culture size or cell number. A system that could accommodate both nitrogen-rich environment for cell replication in logrythmic phase and nitrogen-depleted environments to drive fatty acid synthesis would allow more efficient continuous culture as oppose to limited batch culture. The compartmentalization in relatively small individual photopanels benefits early isolation of problems that may arise such as contamination with viruses, fungi and eukaryotic predators. The establishment of the two functionally different zones, nitrogen-rich vs. nitrogen-depleted zones is also facilitated by the construct of "hollow trabeculae" which further decrease the cross sectional surface area available for diffusion as well as providing the overall structural stability of a thin vertically disposed photopanel. The establishment of the two different functional zones will be further described under methods.

Photobioreactor Structure:

Cost effective photobioreactors or photopanels should be made with common inexpensive and preferably recyclable material like transparent plastics such as but not limited to Polyethylene Terephthalate (PET). The photopanels are vertically disposed. The photopanels should provide containment of an algal culture with an expanded surface area exposed to solar irradiance. Furthermore, the algal culture after taking on the shape of the inner chamber of the photopanel should have a high surface area to volume ratio to facilitate ultra-high cell concentration. The photopanel should be sufficiently thin and tall for the establishment of different functional zones for cell replication vs. fatty synthesis. This is better described as a limited cross sectional area relative to the volume of algae above or below by which the cross sectional area available for diffusion of nutrients, such as nitrogen, to subsequent levels is limited. These objectives are all achieved by the application of a novel construct "hollow trabeculae".

The novel construct of "hollow trabeculae" is inspired by nature. Trabeculae are microbridges such as seen in animal cancellous bone. The trabeculae in cancellous bone stabilize the cortical bone outer surfaces with less bony material and increases the surface area (along the surface area of the trabeculae) for supporting red marrow cells. The idea of small bridges could be applied to give structure to thin plastic membranes or sheets. The simplest manifestation of the trabeculae may be interleaved cones or pyramids. These small bridges or cones can be easily applied to clear plastic by the process of thermoforming. Thin plastic sheets or membranes are heated and made to take on the shape of a mold by vacuum and/or positive pressure. The molded thin plastic membranes with a studded, repetitive, multi-conal structure may then be apposed and fused in a measured and interleaved pattern with an opposing similarly molded plastic membrane or to itself in a clam shape configuration. The "hollow trabeculae" are hollow because this construct represents a negative space. In this conal example, the cones are formed of thin plastic and are filled with only air. The algae culture occupies the narrow space or volume between the cones. The distance between conal sides may be from a few inches to subcentimeter. With a tightly packed conal pattern, the algal culture would take on the desired characteristics of having an expanded surface area with a high surface area to volume ratio. Furthermore, the tight conal pattern also further decreases the cross sectional area available for diffusion of nutrients to other levels within the photopanel to facilitate establishing the two different functional zones.

Climactic conditions and specific algal strain requirements may necessitate thermoregulation of the algae culture. An additional separate outer compartment may be incorporated as one additional layer of transparent material applied to one or both sides of the photopanel to serve as a water bath or jacket. In such case, the "hollow trabeculae" would be filled with circulated water, discontinuous from the algae culture medium. The water jacket could contain a solution that further scatters light if desired.

To clarify the distribution of light over an expanded surface area, simple cones are considered as the "hollow trabeculae" concept. If the amount of light that otherwise illuminate the circle area of a conal base is allowed to strike the larger surface area of the slanted side walls of the cone, that amount of light or number of photons are now distributed over a larger surface area, thereby effectively decreasing the light intensity. The ratio of surface area expansion is related to the ratio of conal height (H) to the Radius® of the conal base. For example, a cone with a conal height (H) that equal the diameter of the conal base or twice the radius of the Conal Base®, translates to approximately 2.2 times increased in surface area from the circular conal base to the slanted surface area of the conal walls. Similarly, conal height H that equal 3® represents expansion of surface area by approximately 3.2 times. Additional surface area expansion can be made with secondary structures on the "hollow trabeculae". This may represent fine surface irregularities on the conal sides or as regular stair-steps. Conceptually, this could be likened to animal intestinal structure, by which increased surface area is desired for higher absorption rates. The "hollow trabeculae", or cones, would be analogous to the primary villi, with the additional conal surface irregularity or stair-steps as secondary villi.

For ease of manufacturing, the photopanel may be made as smaller photopanel component parts that could be assembled into the desired photopanel height. The smaller photopanel components may be manufactured with different surface area expansion ratios and assembled to optimize light intensity for algal photosynthesis relative to the location on the photopanel height as well as geophysical factors. Other manufacturing techniques such as injection molding may also be applied, especially if higher ratios of surface area expansion is desired.

Other elements of the photobioreactor such as sampling, and inlet and outlet ports are for basic utility. Their location may be variable in terms of location either inserted on the narrow sides on the panel or en-face with the face of the photopanel. The importance of the sparger as well as application of nutrients and supplemental artificial light source will be further discussed under Methods.

Deployment Strategy With Sliding/Pivoting Rack System

The global objective of the disclosed novel deployment system for vertically disposed photobioreactors is to optimize the solar irradiance exposed to the algal culture to match the photosynthetic capacity of an algal culture. The disclosed deployment system seeks to optimize the following: 1) consistent and uniform distribution of solar energy among the multiple photosynthetic panels within an algae farm, 2) control of light intensity, and 3) operational practicality. The available solar electromagnetic energy varies tremendously over the hours of the day, as well as seasonal and atmospheric conditions. The emphasis is on limiting toxic high light intensities as damage to the algal photosynthetic apparatus as well as other cell damage and possible cell death, all energetically expensive. During bright sunny conditions, a control mechanism is needed to limit the available light quantities exposed to the algal culture to match the maximum photosynthetic rate of the algal culture is capable of utilizing. Consistent uniform distribution of solar energy to the individual photopanels within a green house or algae farm allows monitoring of just a few representative photopanels. If every photopanel needed to be monitored for pH, nitrate, ammonia, oxygen and CO2, the instrumentation would be prohibitively expensive. With even distribution of solar energy, such that shading from adjacent photopanels are minimized, monitoring of the algae farm may be done with minimal sampling of the central vs. peripheral photopanels. The novel deployment strategy must also allow easy accessibility for maintenance, repair or replacement of the photopanels.

The novel deployment system for vertically disposed photobioreactors or photopanels organizes the photopanels in racks. The racks will have a mechanism to allow translation to improve uniform spatial distribution. The racks in the tight configuration form corridors and allow easy access to the individual photopanels. The limbs on which the photopanels are hung will have a pivot mechanism to control light intensity. With the broad face of the photopanel pivoted parallel, the amount of direct spectral solar irradiance is limited. By deviating slightly off parallel, algal culture exposure to direct solar irradiance could be increased. In other words, light intensity from direct solar irradiance could be dialed up by slight deviation from parallel, less than 5 to 10 degrees, thereby still limiting shading from adjacent photopanels. The solar beams still penetrate the algae farm uniformly, allowing sample monitoring of just a few photopanels. The solar beams that hit the ground treatment are scattered. Typical ground treatment will potentiate the scattering and reflecting of the solar beams, ie low absorption co-efficient. Example of such ground treatment would include but not be limited to white high gloss polyurethane on cement. The scattered light adds to the direct irradiance exposed to the algae culture.

Readily available coating technology will be applied to or in proximity to the physical structure or building that encloses the photopanels. UV-absorbing films would be applied to the physical structure or green house. Movable light diffusion films may also be applied. Consideration for application of such film technology should consider the geophysical location of the algae farm installation. Diffusion films may not be necessary in the equatorial latitudes due to the increase in humidity that causes increased scatter. Similarly, latitudes greater than 40 Degrees also receive significant percentage of scattered light due to a long light path through the atmosphere.

Methods of Operation

General methods of culture to benefit the structural design offered by the novel construct of "hollow trabeculae" are describe in broad conceptual terms to accommodate wide varying culture needs of the diversity of photosynthetic organisms and organelles not limited to eukaryotic microalgae or prokaryotic cyanobacteria. Described methods are meant to illustrate more common application scenarios and not meant to limit other creative applications.

Photosynthetic organisms in aqueous medium are contained within tall photopanels and arranged on sliding and pivoting racks as described above. Both autotrophic and heterotrophic, as well as mixed culture may be applied. Fresh culture medium containing nutrient such as nitrogen (N) and phosphorus (P) are delivered continuously from either the top or bottom ends of the photopanel. The rates of the nutrient delivery, in molar amounts as well as total liquid volume of the fresh medium, are dependent on the photosynthetic activity of the algae culture, the achievable cell concentration for the algal strain and desired rate of harvest. Carbon dioxide ($CO_2$) rich gas is bubbled through the culture from a sparger positioned at the bottom of the panel. Continuous or semi-continuous algal harvest may be from either end of the photopanel, typically opposite end from the delivery of fresh culture media.

Sparger design and selection of bubble size and rate require careful selection. Delivery of $CO_2$ rich gases into the photopanel serves multiple purposes. Beyond delivery of $CO_2$ as a primary nutrient required by photosynthesis, $CO_2$ also serves as a pH buffer. Bubbling also serves in gas exchange of oxygen ($O_2$). Oxygen as a by-product of photosynthesis will accumulate. At high levels, $O_2$ inhibits photosynthesis. Gas exchange of $CO_2$ and $O_2$ are in opposite directions: $CO_2$ out of the bubble and $O_2$ into the bubble as the bubbles rise towards the top. Gas exchange rates are dictated by mass transfer functions. Gas exchange efficiency or rate relates to bubble size. The higher the surface area (SA) to volume ratio, the higher the relative gas exchange rate. As such, smaller bubbles with higher SA to volume ratio have relative higher gas exchange rates. Long circular flow stream are to be avoided, with a preference for localized turbulent flows. The bubble also serves to agitate the cell culture as describe above, causing cells to be exposed to photons, especially in high light conditions with high cell concentrations. The larger the bubble size relates to greater algal cell displacement. Constant agitation by bubbling will also help in limiting biofouling.

High cell concentration culture can be achieved by the structural characteristic of high culture surface area to volume ratio as offered by the tightly packed "hollow trabeculae" novel construct explained above. The high cell concentration culture needs night time support. Because oxygen is a by-product of photosynthesis and often a concern for excessive build up, frequently the need for oxygen in night time algal respiration is forgotten. In low cell concentration cultures or open culture systems, the amount of dissolved oxygen in the culture medium is sufficient for night time respiration of a few cells or there is constant gas exchange with the open environment. In a closed system with ultra-high cell concentration, dissolved oxygen without a constant replenishing source will cause culture collapse.

Night time or dark hour artificial light should be applied at the bottom of the photopanel. The artificial light will drive photosynthesis in the irradiated portion as a replenishing source of oxygen for algae cells in levels above requiring oxygen for night time respiration. $O_2$ from the photosynthetically active lower irradiated zone is transported by bubbling. Bubbling with $O_2$ containing air may be an alternative. Any energy efficient artificial light source may be utilized such as fluorescence, LED and OLED. LED as a currently available technology offers substantial benefits. LED may be 5 times more efficient in generating white light. Furthermore, LED can generate only photosynthetically utilized wavelengths so every photon could be utilized. Additional energy saving may be achieved by reliance on red wavelength photons which require less energy to generate than any other color wavelength. LED lighting also has a longer lifespan, upwards of 60,000 hours. A side-lit light panel utilizing a clear material such as polycarbonate is easily incorporated into the photopanel, either in isolation or part of the containment for thermoregulating water bath or jacket. During day time hours when not in use, the side-lit LED light panels are essentially transparent to allow collection of natural scattered light off the ground, so artificial light sources do not have to be moved around daily.

High cell concentration culture helps establish a nutrient gradient within a tall and thin vertically disposed panel. Rate of diffusion is proportional to cross sectional area available between adjacent levels and concentration gradient. A tall and thin photopanel has a relatively small cross-section area at any level relative to the height, or more specifically the volume, above or below the reference level. The cross-sectional area in the novel photopanel design is further reduced by the tightly packed "hollow trabeculae" construct that also maintain the structure shape, and dimension, of otherwise widening plastic bags that deform to the weight of the high water column.

If nitrogen (N) is continuously administered to an algal culture at either end of the tall photopanels, there is a limited cross sectional area for N to diffuse down a nutrient gradient towards N-depleted zones. Furthermore, N is being consumed by a large number of algal cells as it is diffused to adjacent levels. The higher the cell concentration the higher the number of algal cells consuming the nutrient. As a result, a nitrogen-rich zone at the end of nitrogen administration vs. a nitrogen-depleted zone at the opposite end is established. The transitional zone size is proportional by the cross sectional area and inversely proportional to the cell density concentration of the algal culture. The higher consumption rate from higher cell density culture help negate the stirring effect from bubbling. A N-rich zone is thereby established to optimize cell replication and a N-depleted zone is established to drive fatty acid synthesis.

In the scenario by which a particular desired algal strain is expected to accumulate fatty acid content greater than 50% of it's dry weight and the overall individual cell density becomes less than the density of the culture medium, the algal cells plump with fatty acids would slowly float towards the top of the photopanel, where lipid rich-cells would be continuously harvested. Nutrients including N would be administered at the bottom of the photopanel, where the bottom N-rich environment would potentiate cell replication and the top N-depleted environment would drive fatty acid synthesis. The reverse scenario by which fatty acid-rich cells have individual cell density greater than the culture medium, the lipid rich cells would settle to the bottom of the photopanel where harvesting occurs, and nutrients would be administered at the top of the photopanel. The first scenario is applicable for algal strains selected for or genetically engineered to secret oil droplet into the culture medium. The secreted oil droplets would accumulate at the top of the photopanel to be easily harvested. This novel photopanel design could accommodate suspension cultures as described above as well as possible adherent cultures that some oil secreting strains may be.

Although constant stirring of the algal culture with bubbling may slow biodeposition on the photopanel, biofouling is inevitable, causing light transmission efficiency of the plastic membrane to deteriorate. The preference for a recyclable material such as PET offers the ultimate option of recycling and reforming. Before recycling, the biofilm remaining on an end-of-life photopanel may be utilized to feed concurrent aquacultures such as fish. New coating technologies may also be applied to slow the rate of biofouling. Potentially, two or three crops of different algal strains could be cultivated with optimized pairing of photopanel surface area characteristics and seasonal variablity.

With respect to the above description, before explaining at least one preferred embodiment of the thermoformed vertically disposed system for algae growth herein in detail, it is to be understood that the invention is not limited in its application nor the arrangement of the components or steps set forth in the following description or illustrations in the drawings. The various methods of implementation and operation of the disclosed algae growth system and invention are capable of other embodiments and of being practiced and carried out in various ways which will be obvious to those skilled in the art once they review this disclosure. Also, it is to be understood that the phraseology and terminology employed herein are for the purpose of description and should not be regarded as limiting.

It should be further understood, and those skilled in the art will appreciate, that the conception upon which this disclosure is based, may readily be utilized as a basis for designing of other vertically disposed systems and devices for carrying out the several purposes of the present invention. It is important, therefore, that the objects and claims be regarded as including such equivalent construction and methodology insofar as they do not depart from the spirit and scope of the present invention.

It is an object of this invention to provide photobioreactors which may be constructed at a reasonable cost and can produce products at a cost to compete with current crude oil under normal market conditions.

It is a further object of this invention to provide such a system which will continuously achieve an ultra-high cell concentration algal culture.

It is a further object of this invention to provide such a system which inherently includes means to prevent or limit bio-fouling or deposition of bio-film.

It is a further object of this invention to provide such a system which employs a reactor which is structurally enhanced and concurrently provides a high surface area to volume ratio for the algal culture.

It is yet another object of this invention to provide a desired small cross sectional area for algae propagation which concurrently provides a means for limiting diffusion of nutrient to different height levels for establishing a nutrient gradient.

It is an object of this invention to provide a means for construction and deployment of an algae propagation structure which due to its structural integrity, may be vertically disposed in use and which is materially efficient and cost effective.

Another object of the disclosed invention is the provision of a photopanel which maximizes the collection and conversion of solar electromagnetic energy into biochemical processes through photosynthesis.

Yet an additional object of this invention is the provision of a system which employs a structure which is formed using thermoforming or injection molding, thereby allowing the employment of common, inexpensive and recyclable clear plastic for the formation of highly customizable photopanels.

It is a further object of this invention to apply the disclosed novel concept of interleaved bridging structures, or "hollow trabeculae" which are achievable using thermoforming or injection molding, to provide a means for both stabilization and structural integrity to the otherwise thin plastic membrane material.

It is yet an additional object of this invention to employ the disclosed "hollow trabeculae" to yield multiple functions of structural support while concurrently expanding the algae culture surface area and distribution or scatter of solar irradiance as a means to provide optimized light intensity for algal growth.

It is a further objective of this invention of "hollow trabeculae" to be highly customizable to optimize surface area and light intensity scatter for algae growth through the employment of different ratios of conal height to base diameter. Selection consideration includes position or height level on the photopanel as well as seasonal and geographic solar irradiance differences.

It is a further objective of this invention to provide a means to supplement artificial light to the lower zone during dark night hours through the employment of highly energy efficient artificial light sources such as fluorescent, LED and OLED which are considered important in supporting O2 demand from algae cells in the upper zone experiencing dark conditions and requiring O2 for respiration.

It is a further object of this invention to provide a method to organize and deploy the tall photopanels disclosed herein, using a rack system for supporting the photopanels and a positioning scheme for placement of the racks in a space efficient manner.

It is a further object of this invention to provide a rack positioning method which provides a means for a tight configuration amenable to maintenance and application of supplemental light to the lower zones during night hours, and which will allow for the translation of photopanels into a more evenly distributed pattern during day hours for harnessing of solar energy.

Yet another object of the invention is the provision of photopanel support racks adapted to pivot thereby providing a means to maintain the photopanels substantially parallel with the solar beam to fully control the amount of algae culture exposure to direct solar beam irradiance, and allow for more optimized use of scattered light. The photopanel may be slightly deviated off parallel to dial up higher irradiance from direct solar beam.

Further objectives of this invention will be brought out in the following part of the specification wherein detailed description is for the purpose of fully disclosing the invention without placing limitation thereon.

BRIEF DESCRIPTION OF FIGURE DRAWINGS

FIG. 10-12 depict other shapes and configurations for the projections as "hollow trabeculae" which may be virtually any shape which allows for the structural integrity and enhanced surface area described herein.

DETAILED DESCRIPTION OF THE PREFERRED EMBODIMENTS OF THE INVENTION

Figure 1:
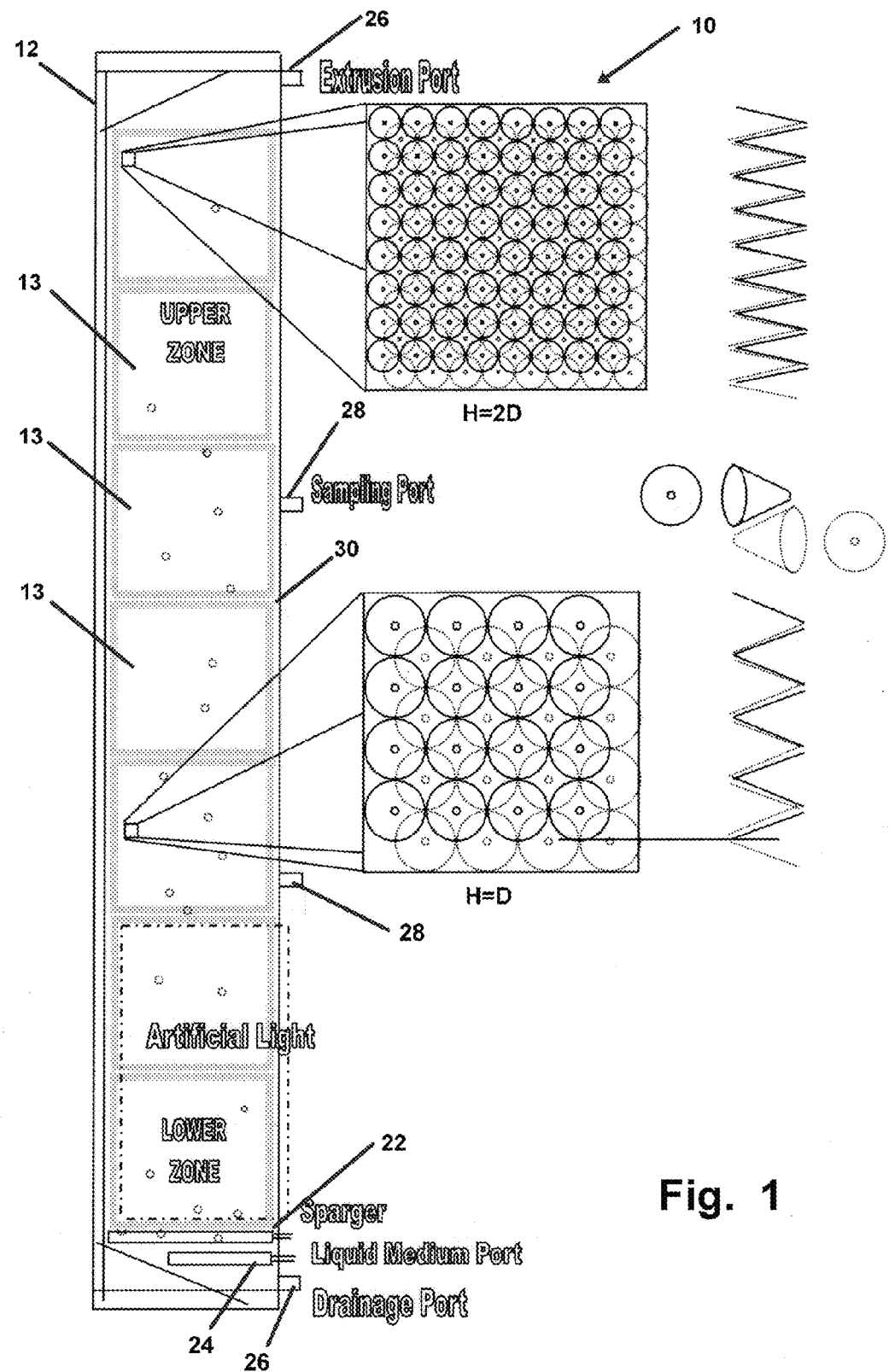
FIG. 1 depicts a typical vertically disposed photopanel, of the disclosed system which is tall and thin "Hollow trabeculae" as key structural elements are represented in the blow up details. The "hollow trabeculae" are represented as conal structures bridging the two faces of the photopanel.

Referring now to the drawings in FIGS. 1-13 wherein similar steps and components are identified by like reference numerals, there is seen in FIG. 1 a typical mode of the device 10 herein, showing a vertically disposed photopanel 12 formed of engaged membranes or segments 13. The photopanels 12 and engaged segments 13 are of a thin clear plastic material which is formed to the proper dimension and shape by any method which will produce the engaged segments 13 forming the photopanels 12 as described herein.

Currently the photopanels 12 are comprised or a plurality of thermoformed segments 13 each having sidewalls 15 (FIG. 9) employing opposing interlocking projections 14 herein referred to as "hollow trabeculae." The distal ends 17 of the projections 14 are configured for a sealed engagement with apertures 19 formed in an opposing sidewall 15 of the formed segment 13. The plastic material should be of conventional inexpensive, preferably recyclable material such as PET, but higher performance materials may be incorporated for specific functions.

Figure 9:
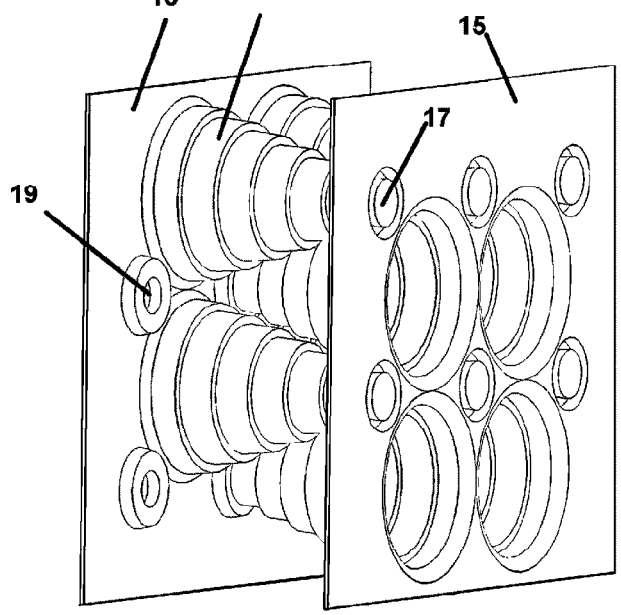
FIG. 9 is an enlarged view of the stepped frustoconical projections as "hollow trabeculae" from FIGS. 7-8 showing the distal end engagement to the opposite sidewall and the greatly increased area of surface for algae propagation such a configuration affords.

The thin plastic segments 13 formed of opposing sidewalls making up the individual photopanels 12, afford the photopanels 12 greatly enhanced structural integrity as well as increased area for algae propagation, by inclusion of these projections 14 (FIGS. 9-11) in a pattern adapted to yield maximum surface area for algae propagation. The engagement of the distal ends 17 of the projections 14 to the opposing sidewall 15 provides a means to maintain the dimension of the cavity formed between the two sidewalls 15 as well as a means to enhance the lateral load carrying ability of the photopanels 12 allowing vertical disposition and use. Without this engagement between the projections 14 and opposing sidewall 15, the photopanels 12 would be subject to deformation of the interior space between the sidewalls 15 as wells as bending from lateral load forces when the thin walled photopanels 12 are employed in substantially vertical positions. The shape of the projections 14 may be of any shape suitable to the installation or task, however a frusto-conical stepped configuration as shown in FIG. 9 is a particular favored mode of the device 10 as it maximizes the interior surface wall of each sidewall 15 where for algal propagation thereon as wells as being structurally quite strong due to the triangular cross section, as opposed to a simple elongated member shape.

The complete tall photopanel 12 is assembled from one or preferably a multiple of interlocking segments 13 to yield the desired height. Each segment 13 is configured with an upper engagement 18 fitting configured for a sealed engagement with a lower engagement 20 fitting of another segment 13 whereby they may be engaged and stacked to form the photopanel 12. The formed photopanel 12 is configured for sealed engagement with a water source to supply necessary fluid to the interior of all engaged segments 13.

The projections 14 or "hollow trabeculae" as conal structures may have different characteristics and may be formed in an infinite number of shapes a few of which are depicted in FIGS. 9-12. As noted the distal ends 17 of the projections 14 engaged an aperture 19 positioned in the opposing sidewall 15 of the segment 13.

While the sidewalls 15 may be formed in any process which yields the correct shapes, thermoforming is currently a favored mode of construction. Molds utilized in the thermoforming process may be built such that each mold may have differing conal height to conal base diameter ratios. The photopanel 12 can then be assembled with a highly customizable series of different trabeculae patterns to optimize light intensity and surface area as relative to available solar irradiance at a particular height. Furthermore the surface of the mold is made irregular with microprotrusions so that the surface of the "hollow trabeculae" provide by the projections 14 in contact with the algae culture is further expanded in terms of surface area in contact.

Specific components as depicted in FIG. 1 such as the sparger 22, liquid medium port 24 and drainage port 26 on the bottom end of the formed photopanel 12, provide fluid flow to the formed photopanel 12 through the engaged plurality of segments 13 forming it. The sparger 22 is operatively connected to a $CO^2$ and or other gas supply and provides the communication of gas bubbles into the medium which flow from the lower zone to the upper zone of the photopanel in normal operations. The extrusion or collection port 26 on the top end of the photopanel 12 which provides the connection to remove algae from the upper zone, and the intervening sampling ports 28 where test samples of the medium may be taken, are incorporated into the spine 30 of the photopanel 12 as area denoted as (A) on FIG. 2. The liquid medium port 24 provides the appropriate nourishing liquid to the medium and the drainage part 26 is employed to drain the photopanel 12 when necessary.

Also shown in FIG. 1, are the projections 14 or conal structures which may be varied in terms of a different ratio between conal height (H) to the circular diameter (D) of the conal base. Two different conal height to base diameter ratios are represented with higher ratio (H=2D) on the upper portion of the panel and lower ration on the lower portion (H=D). Considering a uniform thickness of the photopanel or constant H, the conal circular base of the lower ratio is represented with circular diameter twice that of the higher ratio.

Figure 2:
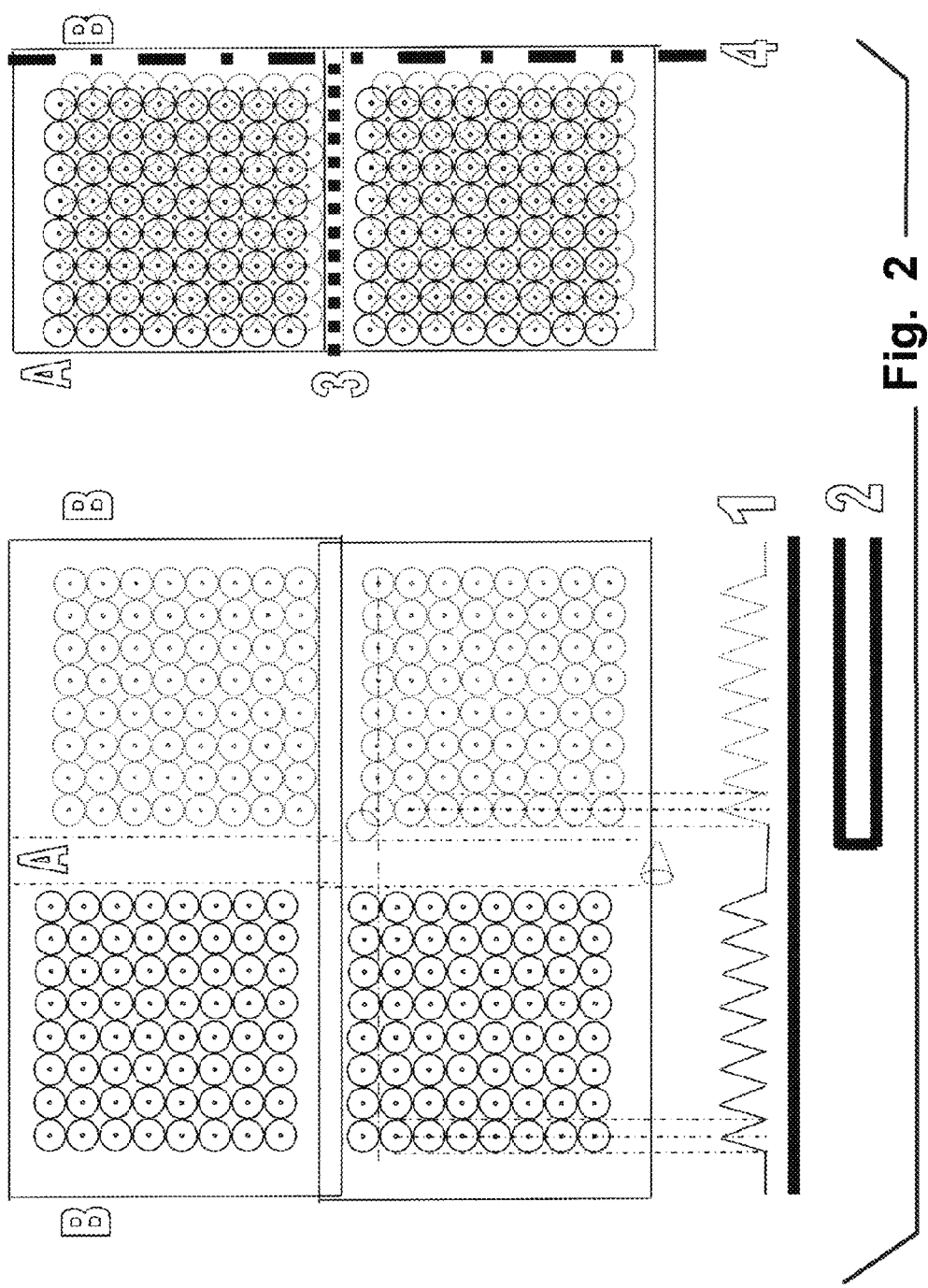
FIG. 2 depicts the process of thermoforming and representative assembly of a typical photopanel.

FIG. 2 depicts the process of thermoforming the sidewalls 15, and representative assembly of a typical photopanel 12. Thin plastic membranes give shape as sidewalls 15, with projections 14 of regular measured conal projections in a tight configuration by thermoforming (1). The plastic membrane forming the sidewalls 15, is folded like a clam shell or book (2). The width of the spine (A) equal the height of the conal projections 14. The distal ends 17 of the conal projections 14 are fused or otherwise engaged to the opposing sidewall 15 in a registered engagement to form the projections 14 in an interleaved fashion. Each such segment 13 may be assembled with other segments 13 by a sealed engagement of the bottom to top edges of subsequent segments. Once all segments are assembled, the remaining open edge (B) is fused.

The formation of the segments 13 in this fashion is inexpensive and allows them to be recycled and reformed when replacements are needed instead of attempting to clean and otherwise maintain segments 13 which have become dirty or where the plastic has clouded over time due to exposure to light. While other plastic material which will not cloud easily in sunlight might be employed, because the thermoforming allows for the plastic to be recycled, and because the engagement of the segments 13 affords an easy manner to form new photopanels 12 it may be much more cost effective to simply recycle the plastic from segments 13 which need maintenance and use newly formed segments 13.

Figure 3:
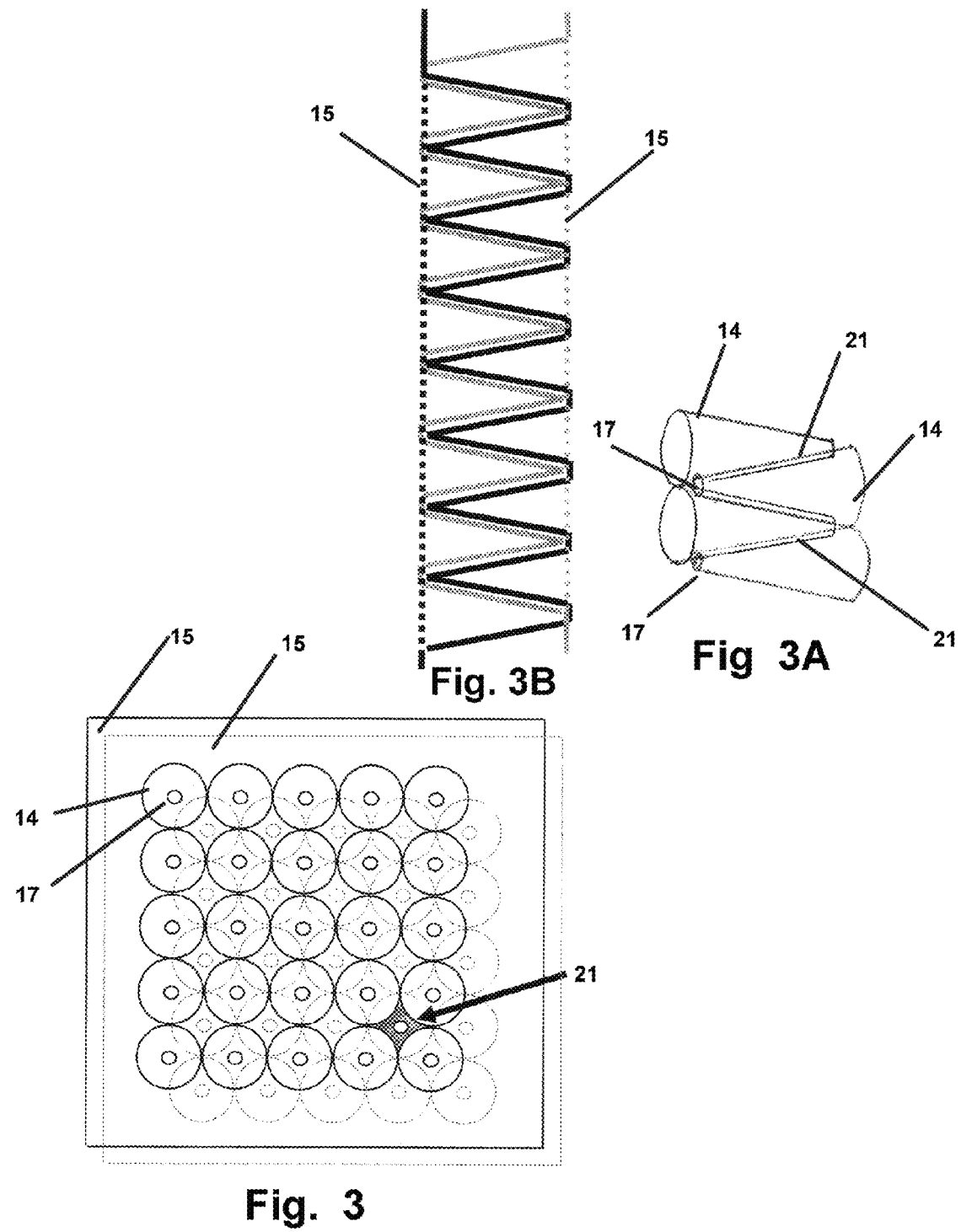
FIG. 3 depicts the shape of the inner chamber of the photopanel as altered by the "hollow trabecular" conal structures.

As shown in FIG. 3, the projections 14 extend in opposite directions from the opposing sidewalls 15 forming each membrane 13 and form thin channels 21 therebetween. The algae culture medium occupies the surface of the interleved projections 14 in the formed thin channels 21 in each membrane. Fluid and gas in the segments 13 flows from the lower end to the upper end of each such segment 13 and follows this fluid flowpath from the lower end of each photopanel 12 (FIGS. 1 and 6) to the upper zone of each photopanel 12. This allows for a constant provision of nourishment to the algae culture occupying the thin channels 21 between the interleaved conal walls of the projections 14.

The most materially efficient and cost effective plastic membrane thickness is selected. In considering the thickness of the sidewalls 15, consideration is made for the support they must provide, further thinning during thermoform of the projections 14 providing the trabeculae, as well as the tension placed on the segments 13 in the vertical orientation as related to weight of the formed photopanel 12 itself as well as the contained culture therein. The thickness of the sidewalls 15 must therefore be able to adequately support the formed photopanel 12, and its contents and is calculable based on the strength of the plastic employed. Similarly, the thinness of the photopanel 12 is optimized with similar considerations, as the thinness is dictated by the height of the trabecular cones formed by the projections 14.

In addition, the thinness of the photopanel 12 as relates to the height of the photopanel 12 is such that a nutrient gradient should be easily established by controlling the administration rate of nutrients at the bottom of the photopanel 12 which flow through each segment 13 to the top end of the formed photopanel 12. Current consideration for the physical dimensions of the photopanels 12 are greater than 16 ft in height and up to 36 ft tall, approximately 4 ft wide for ease of manufacturing and approximate thickness of the segments 12 of up to 6 inches but closer to 1 inch.

Figure 4:
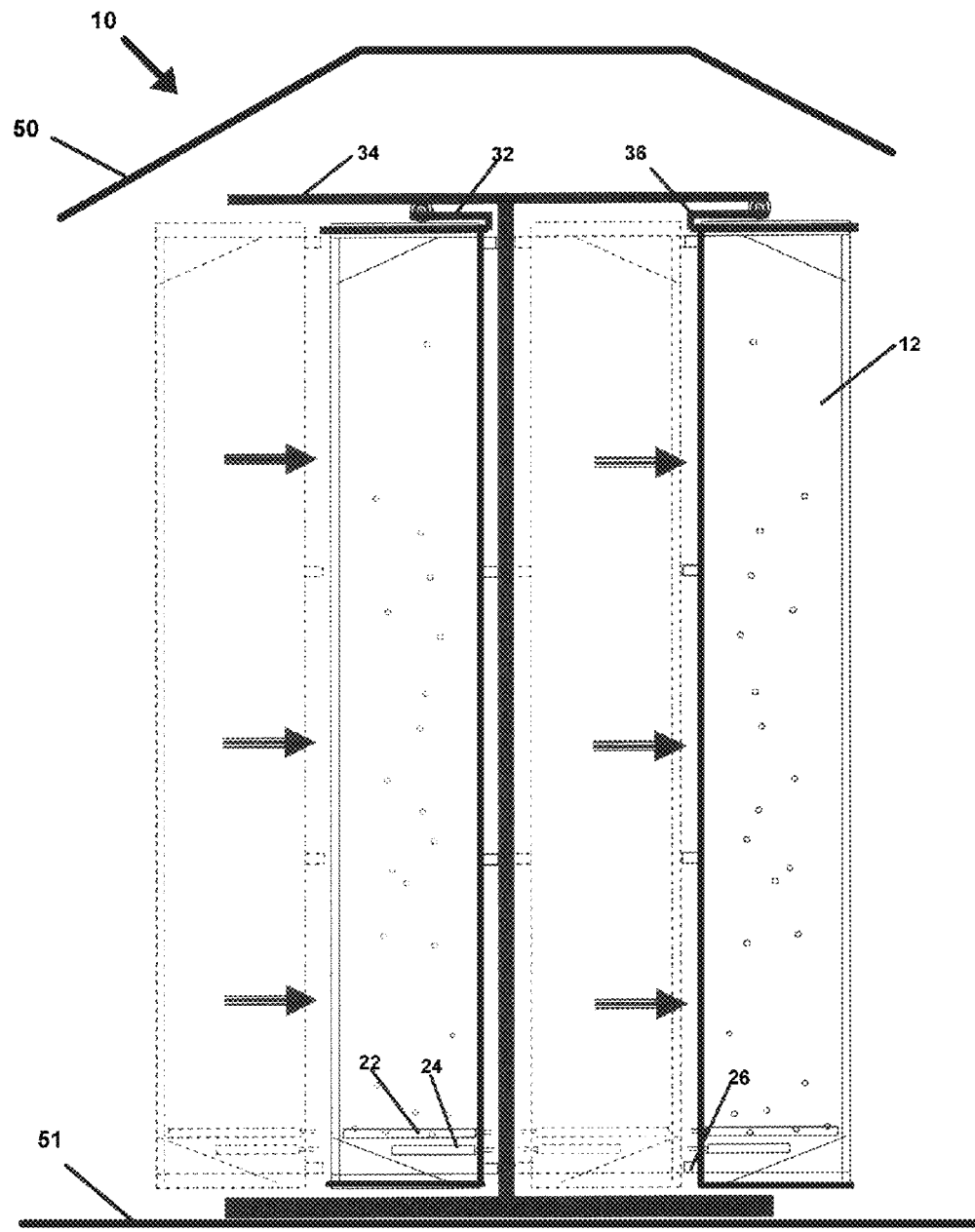
FIG. 4 depicts a representative rack system from a side view demonstrating translating arms.
Figure 5:
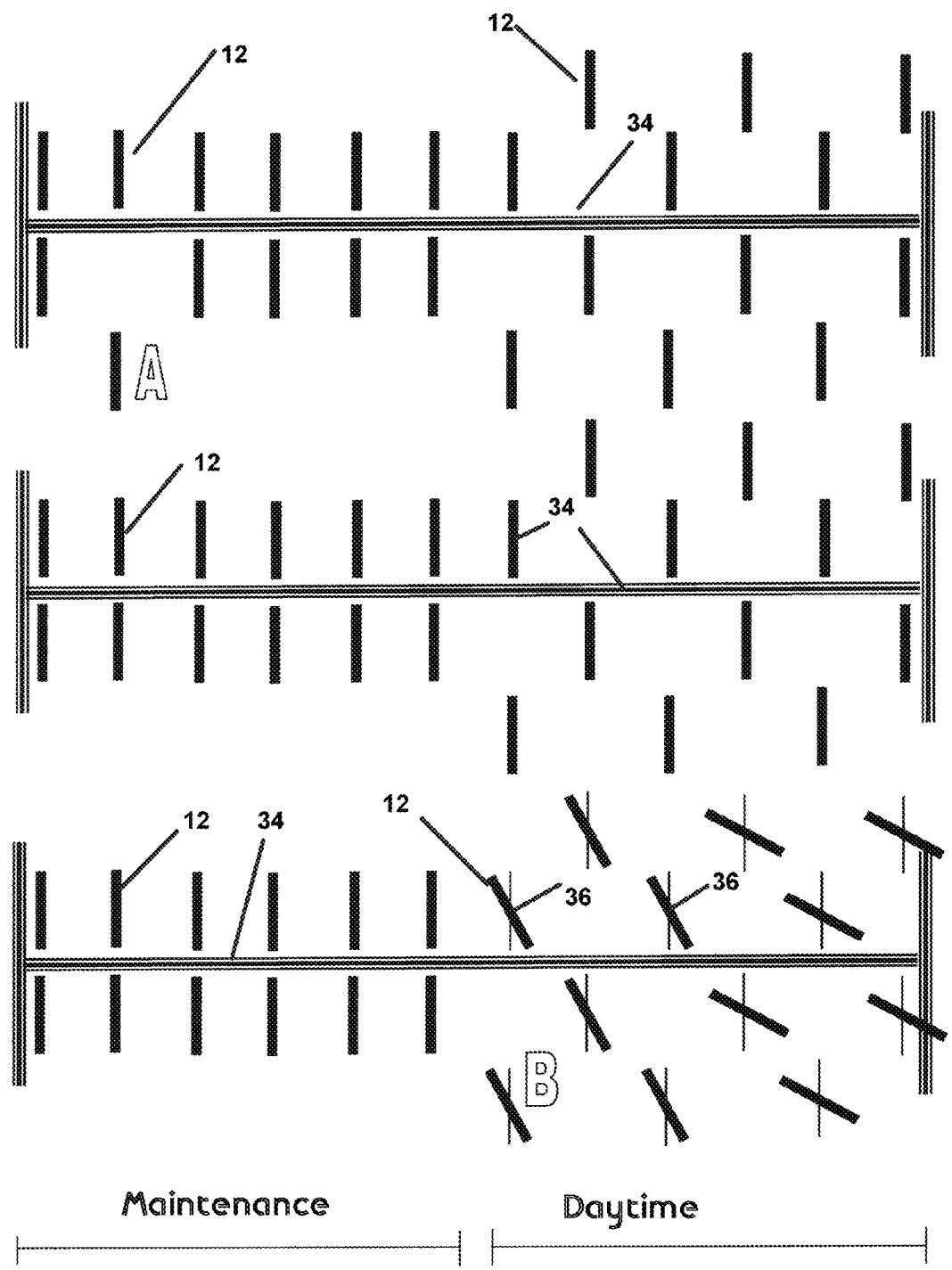
FIG. 5 depicts an overhead plan view of a representative rack system with pivoting and translating mechanisms in different modes of operation pursuant hereto.

The deployment strategy with rack systems of FIGS. 4-5 are made operative through the employment of engaged arms 32 supported by racks 34. The arms 32 provide a means to translate the photopanels 12 on the sliding engagement with the supporting rack 34 and also to rotate on the pivot 36 engagement with the photopanels 12, are depicted in FIGS. 4 and 5.

The deployment ability afforded by the rack system is shown in FIG. 5 wherein the triple lines represent basic rack structure. The bold short lines (A) represent the width of the hung photopanels 12 as seen from an overhead view. As shown, in a night time configuration labeled "A" of FIG. 5 the noted rack system provides a means to translate the photopanels 12 as a means to facilitate the communication of supplemental artificial light, as well as a means to translate the photopanels to positions for maintenance.

The daytime configuration depicted in section "B" employs the provided means for translation of the photopanels 12, to position the photopanels 12 in alternating and/or angled positions to yield a more uniform distribution to each photopanel 12 of incoming light as shown. The translation and pivoting system thereby operates as a means to maximize the positioning of the photopanels 12 for an optimum communication of incoming daylight. Employing the arms of the translating racks and a pivotal engagement, provides a means to angle the photopanels to positions to maintain them substantially parallel to the incoming direct solar beams such as on bright sunny days (B).

Additionally shown in FIG. 4, is the optional roof 50 which may cover the device 10 and operate to diffuse light from the sun. Also depicted is the support surface 51 for the device 10 which may be painted or coated with material adapted to scatter reflected light toward the photopanels 12. The roof 50 and the support surface 51 would be optional enhancements to the performance of the device 10 to users which may be added and adapted for diffusion and scattering ability depending on the terrestrial location of the device 10 and angle of the structure housing the photopanels 12 to the path of the sun thereover.

Figure 6:
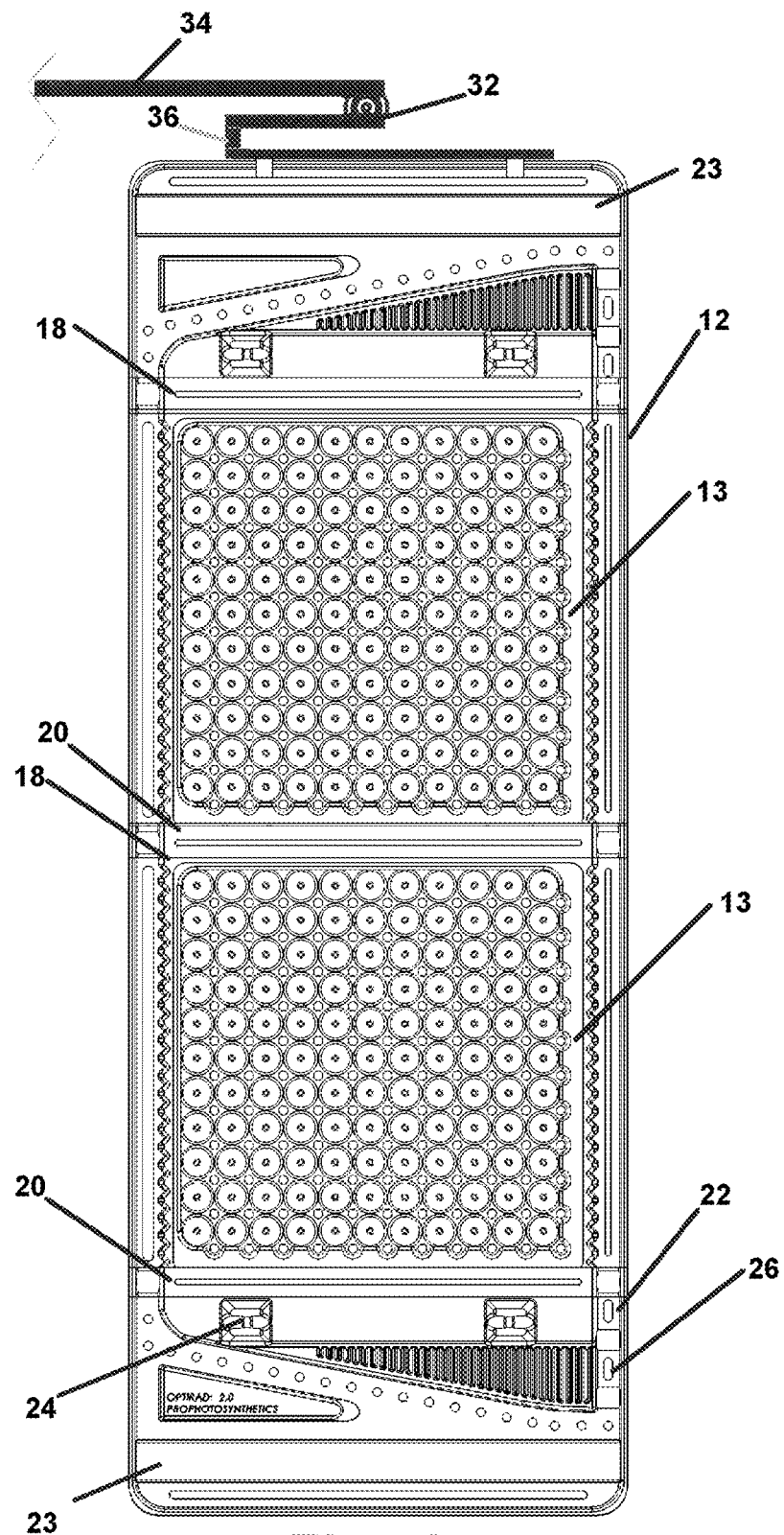
FIG. 6 shows a typical photopanel of the device herein formed on one or a plurality of segments with endcaps engaged and operatively positioned in a translating pivoting engagement, upright to a sliding rack support.

There is shown in FIG. 6 shows a typical photopanel 12 of the device 10 herein formed on one or a plurality of segments 13 with endcaps 21 engaged. The upper engagement 18 fitting of the lower positioned segment 13 is configured for a sealed engagement with a lower engagement 20 fitting of the above-positioned segment 13. This allows the photopanels 12 to be assembled to the desired height using one or a plurality of segments 13 which are placed in a stacked sealed engagement. Fluid and gas flow from the sparger 24 and liquid medium port 22 move from the an area near the lower engagement 20 of the lowest positioned segment 13 up through all segments 13 until reaching the upper engagement 18 of the highest positioned segment 13 and the endcap 23 engaged therein. The fluid and gas flow through the channels 21 in each segment 13 to maintain the growing environment for algae therein at optimum levels. For maximizing light transmission and positioning for maintenance, the photopanel 12 is and operatively engaged upright to support 32 slidingly engaged to a rack 34 with a pivot 36 providing means to rotate the photopanel 12. Of course those skilled in the art will realize that the sparger and liquid medium port may be combined, and that other configurations might be employed for fluid and gas supplies to the photopanel 12 and such are anticipated within the scope of this application.

Figure 7:
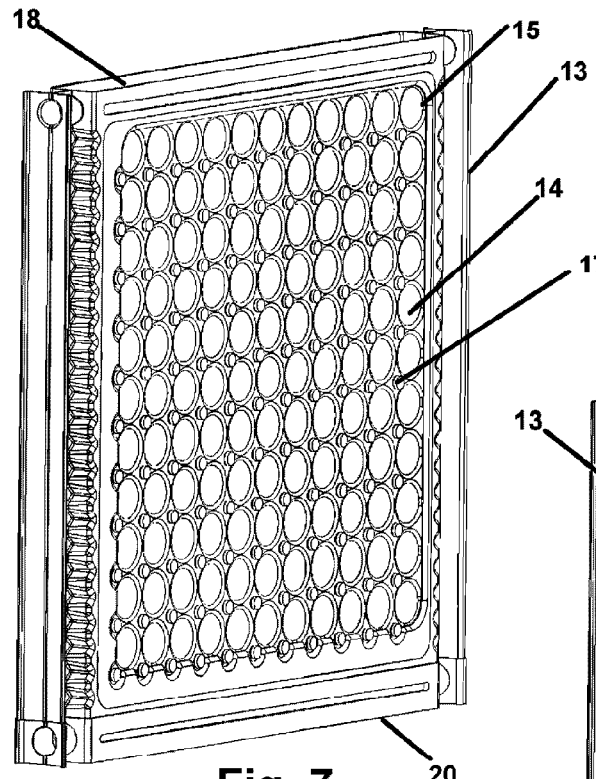
FIG. 7 is a perspective view of a single segment making up the plurality of segments which will form a photopanel herein.

FIG. 7 is a perspective view of a single segment 13 making up the plurality of segments 13 which will form a photopanel 12 herein. As shown, both sidewalls 15 are depicted each with projections 14 which engage apertures at their distal ends 17 in the opposing sidewall 15 which provides exceptional structural integrity to each segment 13.

Figure 8:
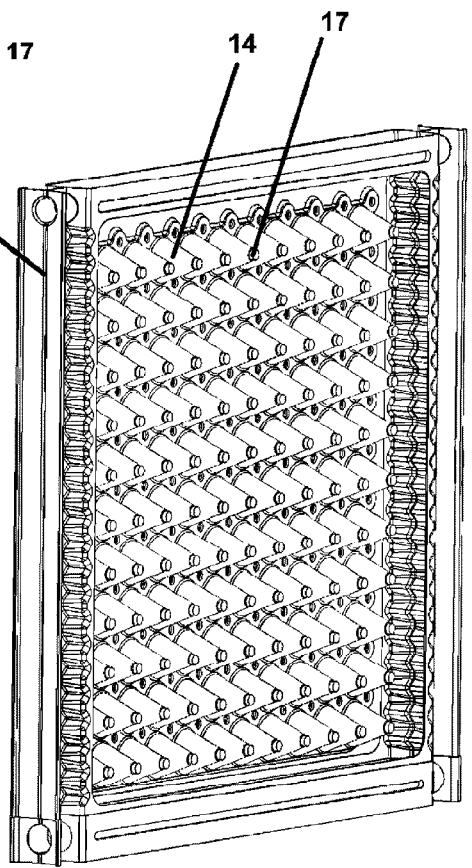
FIG. 8 depicts the segment of FIG. 7 with one sidewall removed showing the plurality of stepped frusto-conical projections which project from both sidewalls to distal ends engaging the opposite sidewall, as "hollow trabeculae".

FIG. 8 depicts the segment 13 of FIG. 7 with one sidewall 15 removed showing the plurality of stepped frusto-conical projections 14 which project from both sidewalls 15 to distal ends 17. The depicted distal ends 17 are in all cases sized to engage apertures 19 or other engagement components in the opposing sidewall 15. Those skilled in the art will realize other means to engage the distal ends 17 of the projections 14 may be employed to achieve the exceptional structural integrity herein and such is anticipated within the scope of this application. However currently the engagement of the distal ends 17 of the projections 14 in apertures 19 or detents in the opposing sidewall 15 is a favored mode of the device 10.

FIG. 9 is an enlarged view of the stepped frustoconcial projections 14 from FIGS. 7-8 showing the distal end 17 engagement to the apertures 19 in an opposite sidewall 15 and the greatly increased area of surface for algae propagation such a configuration affords the sidewall 15 surfaces, while concurrently providing an exceptional increase in structural strength and integrity.

FIG. 10-12 depict other shapes and configurations for the projections 14 which those skilled in the art will realize may be virtually any shape which allows for the structural integrity and enhanced surface area described herein. However the stepped frusto conical shape depicted herein is a current favorite mode of formation of the projections 14.

Figure 13:
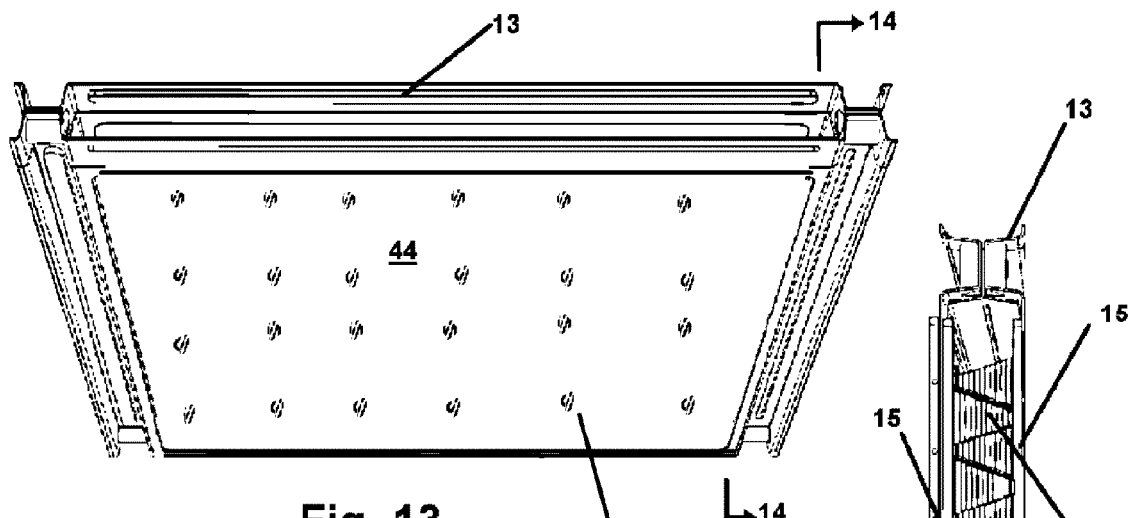
FIG. 13 shows a side-lit LED light panel employed for night time irradiation of the lower zone.
Figure 14:
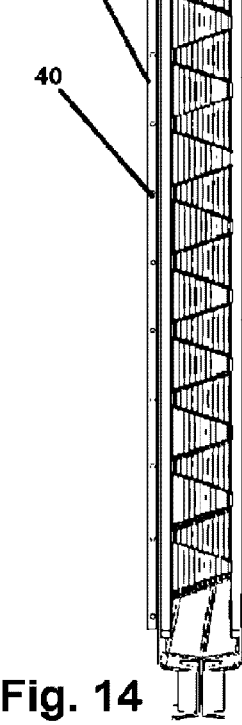
FIG. 14 shows the LED light source engaged to the plastic panel to communicate light to the formed lenses in the central area shown in FIG. 13.

As shown in FIGS. 13 and 14 the system herein additionally may provide means for artificial light transmission to the segments 13 forming the photopanels 12. Currently such artificial light is generated by light emitting diodes (LED's) 40 positioned about the perimeter edge of a clear plastic panel 44. Light from the LED's 40 is communicated into the panel 44 where it travels to positions in the panel 44 adapted to communicate light to the medium within the photopanel 12. In those positions, cutouts or notches 46 are formed in the panels 44 which cause light communicated into the panels 44 to project into the segment 13 and to the medium therein. The clear panel 44 however, does not block any appreciable amount of sunlight or natural light from transmission therethrough and thus allows for full communication of natural light to the medium when not in use.

Figure 15:
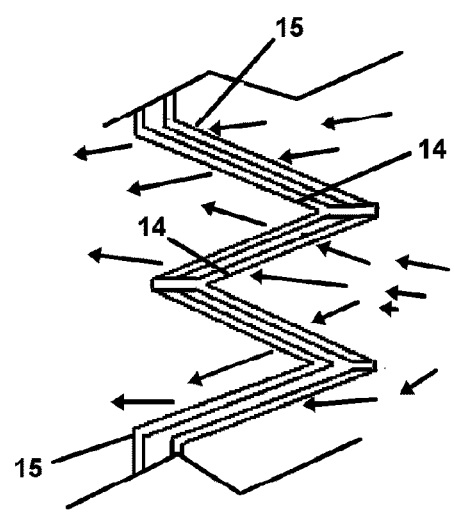
FIG. 15 depicts the enhanced light passage through photopanels of the device having interleved projections with hollow cores formed in sidewalls of substantially equal thickness.

In FIG. 15 there is shown the means for enhanced light passage through photopanels 12 of the device 10 provided by the hollow core sections of the projections 14 providing the increased propagation surface area on the interior of the photopanel 12 on all surfaces. By forming the projections 14 from the sidewall 15 material and leaving a hollow core, light has an uninhibited passage to the interior of the photo panel 12 through sidewall 15 material that is substantially equally as thick in the areas of the projections 14 as the surrounding sidewall 15. Thus light is transmitted through the material forming the sidewall 15 and projections 14 equally well.

While all of the fundamental characteristics and features of the vertically disposed device and method for algae growth been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations are substitutions are included within the scope of the invention as defined by the claims.

What is claimed is:

1. An apparatus configured to contain a light dependent chemical process comprising an enclosure having transparent walls defining an inner chamber to hold a liquid medium, whereby the shape of the inner chamber is structurally stabilized and defined in part or in full by bridging elements formed by integral inwardly projecting extensions of the enclosure walls defining hollow cavities, wherein the hollow cavities are open to the outside of the enclosure at a first sidewall of the enclosure and extend therefrom to planar surfaces of a second opposite sidewall of the enclosure, and said hollow cavities further having truncated ends formed by planar surfaces parallel to the planar surfaces of the second sidewall that directly engage planar surfaces of the second sidewall of the enclosure.

2. The apparatus according to claim 1, wherein the enclosure and the inner chamber form a photobioreactor.

3. The apparatus according to claim 1, wherein the enclosure comprises transparent PET.

4. The apparatus according to claim 2, wherein the bridging elements increase a surface area to volume ratio of the inner chamber.

5. The apparatus according to claim 2, wherein the bridging elements are configured to distribute light to an enlarged inner chamber surface area.

6. The apparatus according to claim 2, wherein the bridging elements form one or more light guides.

7. The apparatus according to claim 2, wherein the enclosure is formed of a plastic film or sheet material that is less than or equal to 0.25 inches thick.

8. The apparatus according to claim 2, wherein the bridging elements are thermoformed with recyclable PET plastic that is less than or equal to 0.125 inches thick.

9. The apparatus of claim 2, wherein at least some bridging elements comprise hollow cones with a base open to the outside of the enclosure.

10. The apparatus according to claim 2, wherein the enclosure has a sufficiently large vertical height and sufficiently small horizontal cross sectional area when vertically disposed and containing a dense cell culture therein to establish a nutrient gradient when a nutrient is applied in one end of the inner chamber.

11. The apparatus according to claim 10, wherein the diffusion of a nutrient is reduced by the presence of the bridging elements, which further decreases or limits the horizontal cross sectional area.

12. The apparatus according to claim 10, further comprising an apparatus for collecting cells, particles, or compositions of matter at one end of the inner chamber.

13. The apparatus according to claim 2, wherein the enclosure has an overall outer shape of a rectangular photopanel with a greater height than width or thickness, wherein the enclosure is formed from one or more vertically extending sections, and wherein the inner chamber contains algae, and wherein the walls of the enclosure are formed of transparent plastic less than or equal to 0.125 inches thick.

14. The apparatus according to claim 13, wherein the walls of the enclosure are thermoformed with transparent recyclable PET.

15. The apparatus according to claim 14, wherein a plurality of hollow cones are thermoformed to the opposing walls of the enclosure as bridging elements.

16. The apparatus according to claim 15, wherein the hollow conal bridging elements increase the surface area to volume ratio of the inner chamber.

17. The apparatus according to claim 15, wherein the hollow conal bridging elements distribute light over the enlarged surface area, and wherein the hollow conal bridging elements comprise smooth or stepped sides.

18. The apparatus according to claim 13, comprising side-lit LED panels applied to one or both sides of the photopanel.

19. The apparatus according to claim 13, wherein the enclosure has an overall rectangular prism outer shape having three dimensions such that a largest dimension of the apparatus is at least 4-fold greater than a second largest dimension, and the second largest dimension is at least 6-fold greater than a third dimension.

20. The apparatus of claim 1, wherein the hollow cavity is wider at the first sidewall than at the second sidewall and wherein the hollow cavity comprises one or more steps between the first sidewall and second sidewall.

* * * * *